United States Patent
Rebholz et al.

(10) Patent No.: US 6,802,974 B2
(45) Date of Patent: Oct. 12, 2004

(54) METHOD AND DEVICE FOR PRODUCING BIOGAS, WHICH CONTAINS METHANE, FROM ORGANIC SUBSTANCES

(76) Inventors: Erich Rebholz, Badstrasse 16, 76571 Gaggenau (DE); Johann Reithmayer, Westernstrasse 62, 85072 Eichastatt (DE)

( * ) Notice: Subject to any disclaimer, the term of this patent is extended or adjusted under 35 U.S.C. 154(b) by 65 days.

(21) Appl. No.: 10/181,548
(22) PCT Filed: Jan. 17, 2001
(86) PCT No.: PCT/EP01/00493
§ 371 (c)(1), (2), (4) Date: Jan. 21, 2003
(87) PCT Pub. No.: WO01/53510
PCT Pub. Date: Jul. 26, 2001

(65) Prior Publication Data
US 2004/0035785 A1 Feb. 26, 2004
(Under 37 CFR 1.47)

(30) Foreign Application Priority Data
Jan. 18, 2000 (EP) ............................................. 00100256

(51) Int. Cl.[7] .............................. C02F 3/02; C12P 5/00
(52) U.S. Cl. ...................... 210/603; 210/620; 210/629; 435/262; 48/127.3
(58) Field of Search ................................ 210/603, 612, 210/620, 629; 435/262, 262.5; 48/127.3

(56) References Cited

U.S. PATENT DOCUMENTS
4,289,625 A  *  9/1981  Tarman et al. ............... 210/603

FOREIGN PATENT DOCUMENTS
| DE | 3330542 | * | 3/1985 |
| DE | 3340971 | * | 5/1985 |
| DE | 3531605 | * | 5/1987 |
| DE | 4103715 | * | 7/1991 |
| GB | 721823 | * | 1/1955 |

* cited by examiner

Primary Examiner—Fred G. Prince
(74) Attorney, Agent, or Firm—Bachman & LaPointe, P.C.

(57) ABSTRACT

A three-stage method used for producing biogas having a high methane content from organic substances includes aerobic fermentation, a charring and thermophilic methane fermentation.

20 Claims, 1 Drawing Sheet

METHOD AND DEVICE FOR PRODUCING BIOGAS, WHICH CONTAINS METHANE, FROM ORGANIC SUBSTANCES

BACKGROUND OF THE INVENTION

The invention entails a method and related mechanism for the production of methane rich biogas from organic materials, more specifically for the production of biogas with a high methane content. In methods of this kind, the organic matter is decomposed by means of living micro-organisms and converted to methane.

Gas, which can serve as an alternative energy source, is generated in the decomposition of organic substances. For reasons of its generation, this gas is described as biogas. An important component of biogas is methane, which originates from organic or vegetal substances or their by-products through fermentation or decomposition under closure from air. In larger production contexts, it is generated through the gasification of coal or in petrochemical processes and is utilised as heating gas and for combustion power, as well as raw material for synthetic products, such as (inter alia) acetylene, synthetic gas, HCN and chlorine substitute products.

Because of methane's importance, it is aimed to achieve a high proportion of methane in the production of biogas. Depending on the level of technology, single or double stage fermentation methods are employed, by which biogas with a methane content of between 40% and 60% is generated from organic material through anaerobic fermentation. The remaining biogas components in these processes consist to between 25% and 55% of $CO^2$, as well as of smaller quantities of nitrogen, hydrogen sulphide and other components.

Hitherto known methods of anaerobic fermentation for the generation of methane from organic materials are therefore not completely satisfactory with regard to the quality of biogas and the volumes of methane produced. Particularly undesirable in these processes is the high proportion of approximately 2% sulphur or hydrogen sulphide, because in concentrations from as low as 0.1%, these are troublesome in the operation of engines and the allied engagement of catalytic converters.

In addition, there are further disadvantages related to known methods of anaerobic fermentation. Thus, the degree of decomposition is usually around 45% of the dry organic substance and the production processes are relatively unstable, as the micro-organisms involved therein are sensitive to environmental changes. A further effect of this is that any discontinuities of the process, such as occurs during servicing intervals or repairs and the subsequent resumption of production, means that profitable productivity levels are only attained some 12 to 25 weeks thereafter.

Furthermore, hitherto familiar technologies leave a non-utilisable residue amounting to about 30% to 70% of the input volumes, which must be rendered free of harmful deposits. Similarly, the conversion time, i.e. the duration between the input of the organic materials to the process and the production of biogas, is relatively long and takes in the vicinity of between 20 and 30 weeks.

The known methods are admittedly environmentally neutral with regard to the carbon dioxide economy, however they do not lead to any reduction in the carbon dioxide burden on the environment. It also remains to be considered that the methane from the unmanaged decomposition in nature is 30 times more negatively burdensome for the greenhouse effect than $CO_2$.

U.S. Pat. No. 4,289,625 describes a bio-thermal gasification method whereby organic matter is initially fermented anaerobically and its residue is then carbonised. The gases formed during carbonisation are then converted to methane by means of anaerobic micro-organisms.

Although the known methods are environmentally neutral in terms of the carbon dioxide economy, they do not lead to a reduction of the environment's carbon dioxide burden. Also to be considered in this regard is the fact that the methane released in the uncontrolled process of decomposition in nature is about 30 times more negatively burdensome than $CO^2$ for the green house effect.

SUMMARY OF THE INVENTION

The object of the invention is to provide a method and related mechanism for the production of methane rich biogas from organic materials by means of which living micro-organisms decompose the latter while delivering a higher margin of methane and simultaneously avoiding or reducing the negative side effects of this state of technology.

The foregoing object is achieved by the present invention by providing a method A method for producing biogas containing methane, comprising: a) contacting organic matter with fermentation micro-organisms under anaerobic fermentation conditions so as to produce residuals and gaseous wastes containing carbon dioxide; b) carbonizing the produced residuals to obtain a charcoal product and wood gas; and c) contacting the wood gas with thermophile fermentation micro-organisms under anaerobic fermentation conditions to produce biogas containing methane and mechanisms for carrying out the method.

BRIEF DESCRIPTION OF THE DRAWING

Preferred configurations and additional developments of the invention will become evident from the subsequent description with related diagrams.

DETAILED DESCRIPTION

Figure 1:
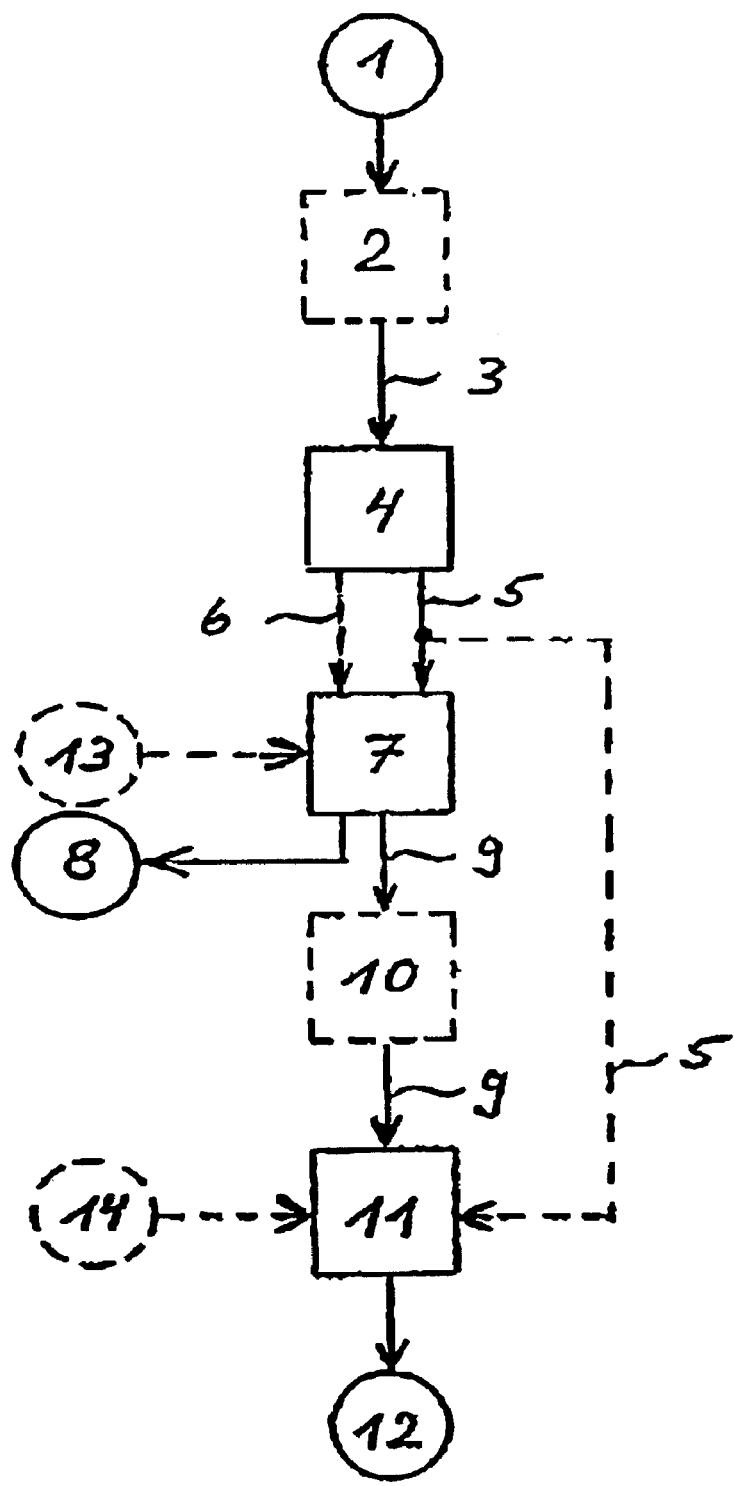
FIG. 1 is a schematic diagram of the method of the present invention.

An inventive method for the production of methane rich biogas from organic matter, whereby such organic matter is decomposed and converted to methane by means of living micro-organisms, therefore encompasses three methodological steps.

In an initial methodological step of aerobic fermentation, organic matter is fermented under aerobic conditions by means of fermentation micro-organisms. In this process, solid and/or liquid residues and gaseous wastes containing $CO^2$ are formed.

In a second methodological step of carbonising, residues from the initial methodological step are burned, such that charcoal or charcoal-like products and wood gas is formed. The residues from the initial methodological step, especially the liquid residues, are dehydrated to facilitate the carbonisation process. To this end, common drying processes are adequate. The water content should preferably amount to less than 20%. The water liberated in the dehydration process can be recaptured in the process of biomass flotation.

In a third methodological step of the thermophile methane fermentation, wood gas from the second methodological step is fermented under anaerobic conditions to methane rich biogas by means of thermophile fermentation micro-organisms.

Fermentation is generally understood to be the decomposition of organic matter by suitable micro-organisms such as yeast cells, bacteria or fungi, particularly moulds. In the initial methodological step of aerobic fermentation, a chemical conversion occurs, i.e. the decomposition of the organic material by suitable fermentation micro-organisms, especially by bacteria. In selecting suitable organisms, it should be considered that fermentation in a liquid nutrient substrate is preferably characterised by a high level of carbon and hydrogen consumption, a strong increase of the micro-organisms and of their conversion products and/or of a microbially converted substrate (e.g. protein enrichment), as well as of the potential for the production of secondary metabolisers (e.g. enzymes, pharmaceutical agents). Examples of suitable micro-organisms are *Aspergillum niger*, *Pyrococcus furiosus* and *Escherischia coli*.

In the initial methodological step, nitrogen is reduced and carbon dioxide is supplemented. The decomposition products essentially include biocarbons, i.e. Ea charcoal-like product, as solid residue, as well as carbon dioxide in the gaseous waste. The biocarbon fermentation product contains large quantities of lignin. By controlling the temperature and the selection of micro-organisms, the fermentation and the dynamics of the conversion process can be managed. The temperature will most advantageously be in the order of between 30° C. and 50° C., and most preferably between 36° C. and 38° C.

In the second methodological step of carbonising, residues from the initial methodological step are combusted after an optional dehydration. Carbonising is understood to mean the heating or slow combustion under controlled air supply reductions or exclusions. In this process, in addition to monomers and dimers, the higher polymers are converted to wood gas and charcoal products. The charcoals thus produced are an end product and can be utilised as may be considered appropriate.

The second methodological step is preferably carried out in a wood gasifier, in which the cyclonic layering method offers particular advantages. Compared with a conventional wood gasification system, this may offer the advantageous feature that—instead of normal atmospheric air—the waste gas from the initial methodological step is recirculated. The application of the $CO^2$ rich waste gases from the aerobic fermentation process in carbonising, especially in the carbonising phase, can be an advantageous feature, because the air volumes formed during the aerobic fermentation are carbon dioxide enriched and nitrogen starved, such that they can be reutilised instead of fresh air in the process of combustion, especially in the carbonising phase. Because the gaseous wastes from aerobic fermentation are carbon dioxide enriched, the carbonisation process is concomitantly enhanced.

The wood gas generated in the second methodological step contains a high proportion of carbon monoxide and carbon dioxide, which are reduced to methane in the third stage of the thermophile methane fermentation.

In the third stage of the thermophile methane fermentation, monomers and dimers, i.e. carbon monoxide and carbon dioxide, are microbially reduced to methane. Where required, chemical and/or physical treatments can also be executed. The micro-organisms that can be utilised in the thermophile methane fermentation should meet the following conditions: a high consumption of $CO^2$ and a strong increase of methane-forming micro-organisms. Examples of such micro-organisms are Methonabaktericum Thermoautrophicum, Methanogascina and Methanococcus.

It may be regarded an additional advantageous feature that other organic materials, especially those containing lignin, can be combusted in the carbonisation process along with the solid and/or liquid residues from the aerobic fermentation.

As yet another beneficial feature, it may be envisaged in thermophile methane fermentation that residues from the aerobic fermentation (after dehydration, if need be) may also be converted together with wood gas from the carbonisation process. In this way, the thermophile methane fermentation can be managed.

According to another advantageous feature, in which management of the thermophile methane fermentation process may also be envisaged, it is suggested that other gases containing carbon monoxide or carbon dioxide may also be fermented to methane together with the wood gas from the carbonisation process in thermophile methane fermentation.

As sources of such gases containing carbon monoxide and carbon dioxide, the following processes can inter alia be considered: incineration processes, e.g. in heating plants or fossil fuel power stations; engine exhaust gases; fermenting processes, e.g. in the brewing industry or yeast manufacturing; carbonisation processes; chemical production runs; natural rotting cycles and industrial processes, as well as fuel cells. This form of execution of the invention thus has the advantage that it is possible to reduce such waste materials to energy rich methane while simultaneously reducing the burden on the environment of carbon monoxide and/or carbon dioxide.

Taking advantage of yet another feature, it is recommended that the thermophile methane fermentation be executed by means of fermentation micro-organisms that thrive optimally in the range between 15° C. and 90° C., preferably between 35° C. and 85° C., but especially between 45° C. and 55° C. or 65° C.

In terms of this invention, a mechanism for the generation of methane rich biogas from organic matter by means of decomposition and conversion through living micro-organisms, in particular for the execution of the method as per the invention, encompasses an aerobic fermentation reactor for the fermentation of organic matter under aerobic conditions by means of fermentation micro-organisms, in which solid and/or liquid residues and gaseous wastes containing $CO^2$ are formed, a carbonising facility for the carbonisation of residues from the aerobic fermentation reactor, in which a charcoal product and wood gas are formed, as well as a methanogenic fermentation reactor for the execution of a thermophile methane fermentation, in which wood gas from the carbonising facility is fermented to methane rich biogas under aerobic conditions by means of thermophile fermentation micro-organisms.

A corresponding plant, e.g. for the generation of electricity from biomass by means of the method invented, is most advantageously configured in size according to the quantities of biomass available. Depending upon the biomass availability, plant sizes of (e.g.) 100 kW, 200 kW, 500 kW, 1 MW or up to about 8 MW are functional. A plant of about 8 MW requires some 100,000 tonnes to 120,000 tonnes of biomass per annum and a space of approximately 10,000 m² to 15,000 m².

The method invented and the concomitant mechanism have the advantage that methane gas with a high methane content in excess of 60% or 70% can be produced. It is possible to configure or develop the technique in such a manner as to produce biogas with a methane content of at least 80%, preferably at least 85% and especially at least 90% in reproducible quality.

The methane is then available as energy carrier or as production material for chemical syntheses. Thus, for instance, the biogas or methane can be utilised in smaller power from heat plants, in gas driven systems or in block heat power stations for the generation of electricity and heat, as well as in gas engines.

An additional advantage of the method invented can be seen in that it can be executed or controlled in such a manner as to produce biogas with an $H_2S$ content of less than 2%, preferably less than 1% and an especially preferred less than 0.5%. As a rule, a sulphur content of less than 0.1% or 0.05% should be the objective. By aerobic fermentation, sulphur is oxidised to sulphate, such that the biogas is almost devoid of sulphur, in contrast to current technology. The methane generated is industrially utilisable.

Furthermore, the degree of decomposition attained by the method invented versus the current state of technology is increased and can reach 65% or more, depending on the organic matter introduced. The microbial processes also run reproducibly and therefore largely without disruption, because the diverse environmental requirements of the micro-organisms can be specifically controlled and contained by means of the invented division of the decomposition of organic matter in aerobic fermentation and anaerobic methanogenesis. The reactivation of a production facility in terms of this invention can therefore reach an economical performance level within not more than eight days. Furthermore, the method invented functions relatively rapidly, such that the processing time for the conversion of an organic material to methane generally amounts to only about 16 to 36 hours, during which peak production of methane is already attained after approximately 12 hours.

The end products of the method invented consist of marketable charcoal as a solid residue and—depending on the raw material utilised—an end product can even be partially reintroduced into the process, i.e. Ea cascading utilisation of the biomass. Economically interesting by-products also derive from the individual processing stages, e.g. pactins, proteins, vegetal drugs, such as hecogenin acetate or acetylsalicylic acid, which may be extracted accordingly.

The method invented only leaves mineral components to an extent of between about 3% to 8% of the organic matter introduced as residuals; these raw materials are deposited.

In additional special forms of. execution, the method can be configured in such a way that additional carbon dioxide is reduced to methane in the thermophile methanogenesis that the $CO^2$ burden on the environment is reduced.

With the invention, therefore, objectives are attained, with which the world of specialists has long been wrestling. In order to aim for exceptional results, the heretofore elucidated preferential features are introduced below in conjunction with more detailed descriptions at the hand of a diagram, exemplary, singular or combinations of executions are illustrated, from which additional beneficial effects may result through the interaction of advantageous features.

FIG. 1 is a diagram of the method invented, alternatively of a related mechanism. The organic matter 1, which serves as raw material, can be any organic matter, i.e. Ea biological organic waste material, e.g. manure, agricultural wastes, clearing mulch, paper mulch, kitchen waste or other waste biomass in bulk.

Organic matter 1 utilisable by the method invented include fuels, biomass and energy plants. Fuels may include wastes from sawmills, wood processing industries or dead wood clearing, agricultural waste, paper, paper mash and organic sludges. Suitable biomass includes e.g. all types of organic waste, such as (e.g.) nutrient residues, including residuals from food production, husks, feed stock wastes, spoilt groceries, abattoir offal, faeces, production residues from starch manufacture, kitchen wastes, etc.

Among specific examples can be mentioned: outdated food stuffs, spelt and grain dust, residues from canneries, molasses residues, dough waste, sludgy wastes, expired confections, tobacco dust, grass, ribs, mulch, cigarette rejects, malt husks, malt sprouts, malt dust, hop husks, fruit, grain and potato peels, drudge and mulches from breweries, grape skins, manufacturing residues from coffee, tea or cocoa processing, yeast or yeast-like residues, feed stock wastes, oil seed residues, fatty wastes (rancid fats), e.g. from slaughter and margarine production; content from fat trimmers; flotation residues; dairy, oil, fat or wax emulsions; production residues from creameries. Sludge from nutrient fat and food oils production; fuller's earth (degreased); bone waste and skin remnants; entrails; poultry waste; fish wastes; stomach, gut and rumen contents; poultry manure; pig and cattle manure; starch sludge; sludge from gelatine manufacture; gelatine mould trimmings; residues from starch production from potatoes, maize and rice; production residues from food oils manufacture and from cosmetic preparations; protein wastes; kitchen and canteen waste (from industrial kitchens, etc).

Possibly utilisable energy plants include (e.g.) China reeds (Miscantus sinensis giganteus), grazing cultures, poplars, sugar cane husks and rapes.

If required, the organic matter 1 can be prepared in an appropriate pre-production stage 2, e.g. by shredding, drying or damping, forming, etc. The organic matter prepared thus 3, is then introduced into the first invented stage, an aerobic fermentation reactor 4, in which a chemical conversion/ decomposition proceeds by means of fermentation micro-organisms, whereby the nitrous content is reduced and the carbon dioxide is enriched.

In this process, solid and/or liquid residues 5 and gaseous wastes containing carbon dioxide are formed. The aerobic fermentation is preferably executed in such a manner as to keep the organic matter moving throughout in order to improve the gains and accelerate the process. To avoid the destruction of micro-organism communities, it is preferable to take care that the organic matter is kept moving without mechanical aids.

A biochemical separation of the organic matter occurs during aerobic fermentation, that offers the micro-organisms in the aerobic methanogenesis stage a better chance of progressive functionality. Furthermore, biomass can be introduced by this process for the purpose of multiple utilisation. For instance, acetylsalicylic acid can in this way be gleaned from grazing culture biomass. Another example is the derivation of pectin from brewery wastes. Yet another example is that whereby hecogenin acetate can be extracted form wastes from sisal fibre manufacture (jute production). By the method invented, the remaining residual substance continues through the process of biogas production.

Another advantageous feature is that it can be preconfigured that the organic matter in the aerobic fermentation reactor 4 is churned up by means of an air supply or pneumatic through-flow system. In this manner, the oxygen is supplied that is required for aerobic fermentation while the organic matter is churned up without mechanical stirring devices.

In the next stage of the method invented, the solid and/or liquid residues 5 are fed into a carbonisation plant 7 subsequent to an optional dehydration. Such a carbonisation plant 7 is preferably a wood gasifier, which preferably functions by the cyclonic layering method. By virtue of another beneficial feature, it may be arranged that the gaseous waste containing carbon dioxide 6 is also fed into the carbonisation process 7, specifically into the carbonising phase, in order to facilitate the carbonisation process or to increase methane delivery.

The carbonising facility 7 produces charcoal 8 as a final product and wood gas 9 that requires further processing and contains high proportions of carbon monoxide and carbon dioxide,—after passing through an optional gas purification process 10—is fed into the third stage of the technique invented, a methanogenesis fermentation reactor 11. The wood gas 6 from the carbonising facility 7 is hot and is preferably fed hot into the methanogenesis fermentation reactor 11. A preferred configuration of a methanogenesis fermentations reactor 11 is a tube reactor.

In the methanogenesis fermentation reactor 11, the wood gas 9 is fermented to biogas 12 with a high methane content by means of thermophile methane fermentation under anaerobic conditions. To simultaneously counteract the destruction of micro-organism communities, it considered an additional beneficial feature that the organic matter in the thermophile methane fermentation is not kept moving by (e.g.) Ea mechanical device.

FIG. 1 also illustrates how it can be considered an additional beneficial feature that further organic materials 13, especially those containing lignin, can be carbonised in the carbonising reactor 7 along with residues 5 from the aerobic fermentation reactor 4.

Illustrated furthermore is how it can be regarded to be yet another added beneficial feature that the methanogenesis fermentation reactor 11 may also be fed residues 5 (alternatively after dehydration) from the aerobic fermentation 4, together with wood gas 9 from the carbonisation for conversion to methane.

A particularly beneficial, optional feature results from the fact that also otherwise sourced gases 14 containing carbon monoxide or carbon dioxide can be fermented to methane together with wood gas 9 from the carbonisation 7.

What is claimed is:

1. A method for producing biogas containing methane, comprising:
    a) contacting organic matter with fermentation micro-organisms under aerobic fermentation conditions so as to produce residuals and gaseous wastes containing carbon dioxide;
    b) carbonising the produced residuals to obtain a charcoal product and wood gas; and
    c) contacting the wood gas with thermophile fermentation micro-organisms under aerobic fermentation conditions to produce biogas containing methane.

2. A method according to claim 1, including the step of keeping the organic matter in motion during the aerobic fermentation.

3. A method according to claim 2, wherein the organic matter is kept in motion by means of air.

4. A method according to claim 1, including the step of adding heretofore a further organic material to the produced residues from the aerobic fermentation in the carbonising step.

5. A method according to claim 1, including the step of adding heretofore a further organic material containing lignin residues from the aerobic fermentation in the carbonising step.

6. A method according to claim 1, including introducing the gaseous waste containing carbon dioxide in the carbonisation step.

7. A method according to claim 1, including introducing residues from the aerobic fermentation step together with wood gas from the carbonisation step in the thermophile methane fermentation step.

8. A method according to claim 1, including introducing other gases containing CO or $CO^2$ together with wood gas from the carbonisation step in the thermophile methane fermentation step.

9. A method according to claim 1, wherein the thermophile fermentation micro-organisms are characterised by optimal living conditions in the range between 18° C. and 90° C.

10. A method according to claim 1, wherein the thermophile fermentation micro-organisms are characterized by optimal living conditions in the range between 35° C. and 85° C.

11. A method according to claim 1, wherein the thermophile fermentation micro-organisms are characterized by optimal living conditions in the range between 45° C. and 65° C.

12. A method according claim 1, wherein the biogas has a methane content of at least 80%.

13. A method according to claim 1, wherein the biogas has a methane content of at least 85%.

14. A method according to claim 1, wherein the biogas has a methane content of at least 90%.

15. A method according to claim 1, wherein the biogas has an $H_2S$ content of less than 2%.

16. A method according to claim 1, wherein the biogas has an $H_2S$ content of less than 1%.

17. A method according to claim 1, wherein the biogas has an $H_2S$ content of less than 0.05%.

18. A method according to claim 1, including providing an aerobic fermentation reactor for the fermentation of organic matter under aerobic conditions by means of fermentation micro-organisms; providing a carbonizing facility for the carbonisation of produced residues; and providing a methanogenesis fermentation reactor for the thermophile fermentation under anaerobic conditions to biogas containing methane.

19. A method according to claim 18, wherein the aerobic fermentation reactor includes means to keep the organic matter in motion.

20. A method according to claim 19, wherein the means includes an air supply for keeping the organic matter in motion.

* * * * *